(12) United States Patent
Xie et al.

(10) Patent No.: US 8,285,491 B2
(45) Date of Patent: Oct. 9, 2012

(54) DEVICES AND METHODS FOR QUANTIFICATION OF LIQUIDS IN GAS-CONDENSATE WELLS

(75) Inventors: Cheng-Gang Xie, Sawston (GB); Paul Hammond, Bourn (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 1121 days.

(21) Appl. No.: 11/915,801

(22) PCT Filed: May 16, 2006

(86) PCT No.: PCT/GB2006/001788
§ 371 (c)(1),
(2), (4) Date: Jul. 14, 2008

(87) PCT Pub. No.: WO2006/129054
PCT Pub. Date: Dec. 7, 2006

(65) Prior Publication Data
US 2009/0216463 A1  Aug. 27, 2009

(30) Foreign Application Priority Data

May 28, 2005  (GB) .................................. 0511030.9

(51) Int. Cl.
*G01N 31/00* (2006.01)
*G01F 1/12* (2006.01)
(52) U.S. Cl. ........... 702/24; 702/100; 702/106; 702/189
(58) Field of Classification Search .............. 702/24–25, 702/50, 100, 106, 155, 188–190
See application file for complete search history.

(56) References Cited

U.S. PATENT DOCUMENTS

| 4,470,697 | A | * | 9/1984 | Chraplyvy et al. ............. 356/73 |
| 4,525,627 | A | | 6/1985 | Krempl et al. |
| 4,563,585 | A | | 1/1986 | Ward |
| 4,874,572 | A | | 10/1989 | Nelson et al. |
| 5,864,392 | A | | 1/1999 | Winklhofer et al. |
| 6,076,049 | A | | 6/2000 | Lievois et al. |

(Continued)

FOREIGN PATENT DOCUMENTS

EP  762107 A1  3/1997
(Continued)

OTHER PUBLICATIONS

Betancourt et al: "Analyzing hydrocarbons in the borehole", Schlumberger Oilfield Review, Autumn 2003, pp. 54-61.
(Continued)

*Primary Examiner* — Phuong Huynh

(57) ABSTRACT

Devices and methods for measuring the fraction of a liquid in a wet gas flow are described, the device including one or more light sources emitting at a first wavelength at which the liquid is highly absorbing and emitting at a second wavelength close to the first wavelength and at which the liquid is not highly absorbing; and one or more sensor for detecting the transmittance of the light at the first and second wavelengths through said gas flow, the device further including processing means for determining a liquid fraction of the liquid in the wet gas flow by correcting the transmittance measured at the first wavelength for the effects of scattering using the transmittance measured at the second wavelength. By making use of cross-correlations or know flow rate meters the device can be used as a flow meter.

13 Claims, 11 Drawing Sheets

U.S. PATENT DOCUMENTS

| | | | |
|---|---|---|---|
| 6,292,756 | B1 | 9/2001 | Lievois et al. |
| 6,707,556 | B2 | 3/2004 | Turner et al. |
| 7,126,687 | B2 | 10/2006 | Hill et al. |
| 2007/0157737 | A1* | 7/2007 | Gysling et al. ............. 73/861.23 |

FOREIGN PATENT DOCUMENTS

| | | |
|---|---|---|
| GB | 1572068 | 7/1980 |
| JP | 5249038 A | 9/1993 |
| JP | 8136445 A | 5/1996 |
| SU | 1154598 A | 5/1985 |
| WO | 0049370 A1 | 8/2000 |

OTHER PUBLICATIONS

Bo et al: "New compact wet gas meter based on a microwave water detection technique and differential pressure flow measurement", North Sea Flow Measurement Workshop, S1. Andrews, Scotland. Oct. 22-25, 2002. paper 4.1.

Busaidi et al: "High water cut: experience and assessment in PDO", SPE Annual Technical Conference and Exhibition, Denver, Colorado, Oct. 5-8, 2003, SPE 84506.

Chraplyvy: "Nonintrusive measurements of vapor concentrations inside sprays", Applied Optics, vol. 20, No. 15,1981, pp. 2620-2624.

Dong et al: "Downhole measurement of methane and GOR in formation fluid samples", SPE 13th Middle East Oil Show and Conference, Bahrain Apr. 5-8, 2003, SPE 81481.

eProduction Solutions: "Red Eye® Water-Cut Meter", Product information: http://www.ep-solutions.com/Solutions/EP/Red_Eye_Products.htm, highlighted item on p. 4, 2008.

Fujisawa et al: "Analyzing reservoir fluid composition in-situ in real time: case study in a carbonate reservoir", SPE Annual Technical Conference and Exhibition, Denver, Colorado, Oct. 5-8, 2003, SPE 84092.

Fujisawa et al: "Near-infrared compositional analysis of gas and condensate reservoir fluids at elevated pressures and temperatures", Applied Spectroscopy, vol. 56, No. 12, 2002, pp. 1615-1620.

Maeda et al: "Near infrared spectroscopy and chemometrics studies of temperature-dependent spectral variations of water: relationship between spectral changes and hydrogen bonds",' Journal of Near Infrared Spectroscopy, 3. 1995. pp. 191-201.

Mehdizadeh et al: "Wet gas metering: trends in applications and technical developments", SPE Annual Technical Conference and Exhibition, San Antonio, Texas, Sep. 29-Oct. 2, 2002, SPE77351.

Mullins et al: "Linearity of near-infrared spectra of alkanes", Applied Spectroscopy, vol. 54, No. 4, 2000, pp. 624-629.

Schroder et al: "Infra-red differential absorption analysis for monodisperse aerosols", Journal of Aerosol Science, vol. 9, 1978, pp. 321-329.

Segtnan et al: "Studies on the structure of water using two-dimensional near-infrared correlation spectroscopy and principal component analysis", Analytical Chemistry, 73, 2001, pp. 3153-3161.

Smith: "Void fractions in two-phase flow: a correlation based upon an equal velocity head model", Proc. Instn Mech Engrs, vol. 184, pt. 1, No. 36,1969-70, pp. 647-664.

van Agthoven et al: "Near-infrared spectral analysis of gas mixtures", Applied Spectroscopy, vol. 56, No. 5, 2002, pp. 593-598.

* cited by examiner

DEVICES AND METHODS FOR QUANTIFICATION OF LIQUIDS IN GAS-CONDENSATE WELLS

CROSS-REFERENCE TO RELATED APPLICATIONS

This application claims the benefits of priority from:
i) Application Number 0511030.9, entitled "DEVICES AND METHODS FOR QUANTIFICATION OF LIQUIDS IN GAS-CONDENSATE WELLS," filed in the United Kingdom on May 28, 2005; and
ii) Application Number PCT/GB2006/001788, entitled "DEVICES AND METHODS FOR QUANTIFICATION OF LIQUIDS IN GAS-CONDENSATE WELLS," filed under the PCT on May 16, 2006;
All of which are commonly assigned to assignee of the present invention and hereby incorporated by reference in their entirety.

The present invention relates to devices and methods for quantification of liquids in gas-condensate wells. It is particularly, but not exclusively, concerned with devices and methods for measuring water and condensate holdup in wet-gas flows.

BACKGROUND OF THE INVENTION

For wet-gas flows under very high gas-cut conditions (e.g. gas volume fraction (GVF)>99%), it has proven difficult to measure, in-line, very small amounts of liquids and the water-in-liquid ratio (WLR), by using dual-energy nuclear measurement technology. For subsea gas wells, for example, it is important to detect, close to the wellhead, the first onset of water and also to quantify water flow rate, in order to provide an early warning of hydrate plugging and corrosion to long subsea flowlines and to control the injection rate of hydrate and/or corrosion inhibitors.

Differentiation between different liquids in a gas stream, such as condensate and water in a gas-condensate well, is also invaluable for the economics of a gas well and for the planning of liquid handling facilities at surface. This is because condensates can provide a large portion of the economic value from a gas well (e.g. a gas well with a flow rate of up to 100 MMscf/day and with condensate-gas-ratio (CGR) up to 200 bbl/MMscf, will produce up to 20,000 bbl/day of condensate).

Most commercial wet-gas flowmeters use a differential pressure device plus another sensing technology to measure gas and liquid flow rates, for example as described in P Mehdizadeh et al. "Wet gas metering: Trends in applications & technical developments", Society of Petroleum Engineers (SPE) 77351 and Ø.L.Bø, et al. "New compact wet gas meter Based on a microwave water detection technique and differential flow Measurement", North Sea Flow Measurement Workshop, 22-25 Oct., 2002.

There have been two directions in developing high GVF wet-gas flow meters:
  Development of correction factors for gas flow rate metering for single-phase gas flow meters (such as orifice, Venturi, V-cone, Coriolis and ultrasonic) when a small amount of liquid is present; and
  Use of hybrid in-line multiphase flowmeters having gas-liquid separation technology, to handle very high GVF multiphase flows. This however tends to yield bulky and expensive devices.

Extension of existing flow meters to 3-phase capability and quantification of the WLR of the liquid phase in a wet-gas stream are thus desirable.

Three techniques are currently used to determine holdup and/or WLR: single- or dual-energy nuclear, electromagnetic (microwave, capacitance-conductance) and optical (e.g. infrared).

Roxar has deployed microwave sensors for water holdup detection for subsea gas wells: see Ø.L.Bø, et al. referenced above.

Based on sensing narrow-band near-infrared (NIR) optical bulk transmission through an oil/water mixture flowing in a narrowed gap, eProduction Solutions have used the Red-Eye™ water-cut meter (of former Premium Instruments) for measuring the WLR of liquid-rich (oil/water) flows. The Red-Eye device is stated to be an embodiment of U.S. Pat. No. 6,076,049B and is essentially an oil-fraction meter; the light emission centred at 950 nm wavelength is substantially transmitted through water phase and gas phase and is substantially absorbed by oil phase. Light emission at a second wavelength of 1140 nm is also disclosed; this is substantially absorbed by oil content and water content, and substantially transmitted by gas content. The narrow band water-cut meter is said to yield a full range water-cut detection independent of entrained gas. To measure accurately the transmittance at 950 nm, detectors are used to measure the directly transmitted light across the narrow flow gap, and also the light scattered forward and backward across the gap.

However, the Red-Eye meter is stated to be unsuitable for high gas flow (see a description of the Red-Eye meter at http://www.ep-solutions.com/PDFs/eP_L/L_Red_Eye_Water-Cut_Meter.pdf).

The performance of the Red-Eye water-cut meter has been reported in SPE 84506 "High-Water Cut: Experience and Assessment in PDO" (SPE Annual Technical Conference and Exhibition held in Denver, Colo., U.S.A, 5-8 Oct. 2003). The water-cut accuracy of the Red Eye meter was found to be within +/−1% absolute in oil/water flow for water cut between 85% and 100% with a confidence level better than 90%. In oil/water/gas flow (GVF=<25%), the accuracy was within +/−2% absolute with a confidence level better than 90%. The Red Eye meter exhibited large error (up to 20% absolute) at lower water cut, and also at low flow rate (gross of 200 m³/d). The latter was due to the flow not being properly mixed.

U.S. Pat. No. 6,292,756 B1 discloses a narrow-band infrared water fraction meter for use with gas wells (and for liquid hydrocarbon flows). The narrow band light emission centered at a wavelength of approximately 1450 nm is substantially transmitted through the gas phase and condensate (liquid hydrocarbon) phase of a flow stream and is substantially absorbed by the water phase of the flow stream (this is consistent with the fluid optical spectral properties shown in FIG. 1). The narrow-band infrared water fraction meter is said to provide water fraction detection independent of entrained condensate. There are no published test results or commercial products for water fraction detection of wet-gas flows based on narrow-band optical transmission measurements at a wavelength around 1450 nm.

One particular problem associated with measurement of optical transmission through a multi-phase flow stream is the scattering of the optical beam by a number of different mechanisms, in addition to any absorption by the phases.

SUMMARY OF THE INVENTION

In its broadest aspects the invention provides methods and devices for analysing in-line (full-bore) multi-phase flows which correct for the effects of scattering on the measurement process.

According to a first aspect the present invention provides a device for measuring the fraction of a liquid in a wet gas flow, the device including:
- one or more light sources having emissions at a first wavelength, at which the liquid is highly absorbing, and at a second wavelength, at which the liquid is not highly absorbing and which is preferably close to the first wavelength; and
- one or more sensors for detecting the transmittance of the light at the first and second wavelengths through said gas flow,
- the device further including processing means for determining a liquid fraction of the liquid in the wet gas flow by correcting the transmittance measured at the first wavelength for the effects of scattering using the transmittance measured at the second wavelength(s).

The device may thus allow accurate quantification of the fraction ratio (such as WLR) of one or more liquid phases by correcting for the effects of scattering on the measured transmissions.

The liquid detected may be water and said first wavelength is then preferably about 1450 nm. As shown in FIG. 1, water has an absorption peak at 1450 nm at standard pressure (about $10^5$ Pa) and temperature (about 20° C.). These ranges can shift depending on temperature and/or pressure. For example, at ambient pressure, water O—H band shifts from 1460 nm to 1424 nm as the temperature is increased from 5 to 85° C. The absorption peak strength changes by about 10% relative [see V. H. Segtnan et al. "Studies on the structure of water using two-dimensional near-infrared correlation spectroscopy and principal component analysis", *Analytical Chemistry* 73 (13): 3153-61 July 2001]. The spectra difference at the isosbestic point of 1446 nm is close to nil [see H. Maeda and Y. Ozaki "Near infrared spectroscopy and chemometrics studies of temperature-dependent spectral variations of water: relationship between spectral changes and hydrogen bonds", *J. Near Infrared Spectroscopy* 3 191-201 1995]. Over the temperature range of 5 to 85° C., it seems advantageous to measure water absorption at the isosbestic point wavelength of 1446 nm for water fraction determination.

The liquid detected may alternatively be condensate and said first wavelength is then preferably obtained by sample fluid calibration. For example, condensate shown in FIG. 1 is highly absorbing at about 350 nm.

Preferably said second wavelength is within 20% of the first wavelength, and more preferably it is close to the first wavelength, whilst being such that the liquid being measured has reduced optical density at that wavelength.

By keeping the two wavelengths used in the device relatively close to each other, the impact of wavelength dependent scattering on the measurements at each wavelength can be minimized.

Where the liquid detected is water, said first wavelength is preferably about 1450 nm and said second wavelength is preferably in the range of about 1200 nm to about 1300 nm. Where the liquid detected is condensate, said first wavelength is preferably obtained by sample fluid calibration, and may be about 350 nm for the condensate example shown in FIG. 1, in which case said second wavelength is preferably about 500 nm. Typically where the liquid detected is condensate, said first wavelength is in the range of about 250 nm to 450 nm, and said second wavelength is in the range of about 450 nm to 600 nm.

Preferably the first and second wavelengths are chosen such that there is a difference of at least 2 between the optical density of the liquid at each of those wavelengths, when measured along a 2 mm optical path length.

Since optical density is measured logarithmically and is proportional to the optical path length, if there is a difference of 2 in the optical density of the liquid at the wavelengths and the path length in question, the absorption at the second wavelength will be 1/100th of that at the first wavelength, and thus the principal impact on transmittance at the second wavelength will be scattering.

It may be desirable to choose the wavelengths to achieve a balance between the differences in optical density of the liquid (which will generally increase with an increasing difference in wavelength) and the change to the scattering effect caused by the difference between the wavelengths.

To realize in-line (or full-bore) optical liquid fraction detection, preferably the path length between said light sources and said sensor is at least 5 cm. In some embodiments the path length between the light sources and the sensor may be at least 10 cm. If the apparatus is arranged to measure liquid fractions in a flow which is primarily (generally >99%) gas, then absorption of narrow beam light sources by the liquid fractions should be sufficiently small to allow the light sources and the sensor to be positioned across the diameter of a standard pipe (e.g. 2 inch or 4 inch, or larger). However, the devices and apparatuses of the present invention are equally useful when applied to small pipe diameters, such as in a downstream sample flow line. It is for example feasible to apply the present invention to a smaller flow line, e.g. a 1 mm path length optical sample flow cell for use with calibrating the absorption spectra of sampled condensate and water fluids at line pressure and temperature condition.

Preferably the flow through the device is substantially vertical. This can mean that the flow is generally annular-mist flow, axi-symmetric along the path between the light sources and the sensors.

In circumstances where transmission attenuation caused by the scattering of the entrained liquid droplets is overwhelming, the flow through the device is preferably substantially horizontal. This can mean that the liquid is generally formed as a stratified film moving along the bottom of the pipe. In such arrangements the light sources and the sensors may be aligned along the height of the liquid film (i.e. substantially vertically). Alternatively or in addition to a horizontal alignment, the flow upstream of the measurement section can be swirled to throw the droplets onto the pipe wall; this can also reduce the number of droplets and hence the scattering.

The light source required for the device may comprise a light emitter capable of emitting over a broad spectrum. To derive transmittance at specific wavelengths, it is possible to employ known spectroscopic methods and equipment to either limit the emission at a given time to a narrow band of wavelengths or use the full spectrum of the source and adapted the detection so as to limit detection to two or more narrow wavelength bands. Alternatively the detectors may be adapted to provide a spectrally resolved signal, i.e. at least a partial transmission spectrum. When spectroscopic measurements are taken, the wavelengths used for measurements according to the present invention can be selected or adjusted depending on those spectroscopic measurements using for example a device wherein the first and second wavelengths are preferably characterized by performing periodic absorption spectra measurement of sampled single-phase fluid flowing through an optical flow cell, under line pressure and temperature.

In an alternative embodiment of the invention, the light source may include two or more narrow band light emitters that emit light at specific wavelengths. The narrow band light sources are preferably light-emitting diodes (LEDs) or laser diodes (LDs), more preferably the LEDs or LDs are arranged so that their operating temperatures are kept substantially constant to maintain their emission peak wavelengths.

In embodiments of the invention, the light sources are provided by a single source which is capable of narrowband emissions at more than one wavelength (e.g. a combined-LED or -LD source). In one particular embodiment a light source which is capable of emitting across a range of continuous wavelengths is used.

Preferably the light source(s) emit in a pulsed fashion and the sensor means or processing means includes a phase-lock device to lock the frequency of the detected signal to the pulsing frequency of the emitted signal.

In such an arrangement, the light source(s) may emit in a pulsed fashion at different pulse frequencies to each other. This may allow the phase-lock device to readily distinguish signals at one wavelength from those at another wavelength. This arrangement may be particularly useful in embodiments which use combined narrow-band LEDs or LDs in a single light source.

The sensor preferably includes one or more photodiodes, or an array of photodiodes in particular for embodiments with spectroscopic measurement using grating spectrometers.

A second aspect of the present invention provides an apparatus for measuring the fraction of two liquids in a multi-phase wet-gas flow, the apparatus including two devices according to the first aspect above, each of said devices being arranged to detect a respective one of said liquids.

The or each device of the second aspect may include any combination of the optional or preferred features of the devices of the first aspect.

Preferably, a first of said devices is a water detector unit with a first wavelength of about 1450 nm and a second of said devices is a condensate detector unit with a first wavelength of about say 350 nm (depending on the calibration spectra for the specific condensate). By measuring the fractions of water and condensate in a multi-phase flow, the total liquid fraction in the flow can be calculated. Such measurements may also be used in calculating overall and individual phase flow rates of the multi-phase flow.

Although the two devices of this aspect need not be located immediately in succession along the flow path, such an arrangement is preferable as it means that the flow pattern through both devices is substantially similar.

In embodiments of the invention, the light sources of both of the two devices may be provided by a single source which is capable of emissions at more than one wavelength. More particularly a single light source which is capable of emitting across a range of wavelengths may be used to provide the light sources of both of the devices. Again, use of a light source with a broad emission spectrum may allow spectroscopic measurements to be taken.

In a development of the above aspects, the invention envisages the use of cross-correlation to improve the flow rate measurements as performed using one of the above embodiments. According to two principal variants cross-correlation can be established either between any of the transmission measurement and at least one additional sensor arranged at an angle to the transmission path of at least one of said light sources to detect scattered light. Alternatively, cross-correlation can be established between the measurements measuring the fraction of two liquids in a multi-phase wet-gas flow, using the two devices according to the first aspect of the invention.

Preferably the apparatus or device thus includes at least one, more preferably at least two additional sensors arranged at an angle to the transmission path of a light source to detect scattered light. Preferably, the light source and the respective sensors for transmission and scattering are arranged in a plane perpendicular to the pipe.

The apparatus may further comprise processing means for determining a correlation or measuring the cross-correlation between the levels of scattered or transmitted light detected by the sensors at different positions along the gas flow.

When employing the second variant of cross-correlation, the light sources and detectors used for transmission measurements can be used for the correlation measurements.

Alternatively or additionally an additional "scattering" sensor may be provided in each device and the cross-correlation of the scattered measurements determined.

This measured cross-correlation may be used to determine a flow rate of the gas flow, e.g. by determining the time interval between correlated events and comparing this to the distance between the sensors. The processor may thus be further adapted to determine a flow rate of the gas flow itself, or of any entrained liquid, or of a liquid film formed on the pipe wall from the measured cross-correlation.

Therefore it is a further aspect of the present invention to provide an apparatus for determining a flow rate of a gas flow or a component of said gas flow, including:
  one or more light sources having emissions at a first wavelength, at which the liquid is highly absorbing, and at a second wavelength, at which the liquid is not highly absorbing and which is preferably close to the first wavelength; and
  a sensor for detecting the transmittance of the light at the first and second wavelengths through said gas flow,
  the device further including processing means for determining said flow rate by cross-correlating the detected transmittance or scattering of light from said first and second light sources.

Said flow rate may be a flow rate of a liquid film, e.g. on a pipe wall, or a flow rate of liquid entrained in said gas flow. In preferred embodiments, the processing means is adapted to determine more than one flow rate which may include either or both of the above flow rates.

Preferably the flow is at least 95% gas by volume.

Other known types of flow rate meters can be used to establish a flow rate. For example variants of the present invention can be combined with a venturi-type flow meter to further improve the measurements of wet-gas gas and liquid flow rates, especially for dry gas and extremely uniformly-distributed wet-gas flows (such as those containing water vapor) where cross-correlation method fails to work.

Hence, it is a further aspect of the present invention provides a surface flow meter incorporating the device or the apparatus of any of the above aspects, with optional and preferred features corresponding to the optional and preferred features described in relation to those aspects.

The light sources and related elements of this aspect of the invention can be any of those described above with respect to the first and second aspects of the invention.

Another aspect of the present invention provides a method of measuring a fraction of a liquid in a wet-gas flow, the method including the steps of:
  detecting the transmittance of light at a wavelength at which the liquid is highly absorbing;
  detecting the transmittance of light at a second wavelength which is close to the first wavelength and at which the liquid is not highly absorbing;
  correcting the transmittance measured at the first wavelength for the effects of scattering using the transmittance measured at the second wavelength(s); and calculating a liquid fraction of the liquid in the wet gas flow from the corrected transmittance.

Preferably the method of the present aspect includes using an apparatus according to the first aspect above, with or without any or all of the preferred or optional features of that aspect.

As described above with respect to the apparatus, the liquid may be water and said first wavelength is then preferably about 1450 nm. Water shows an absorption peak at 1450 nm at standard pressure (about $10^5$ Pa) and temperature (about 20° C.). The liquid may be condensate and said first wavelength is then preferably obtained by sample fluid calibration. For example, condensate shown in FIG. 1 is highly absorbing at about 350 nm.

Preferably said second wavelength is within 20% of the first wavelength, and more preferably it is as close as possible to the first wavelength, whilst being such that the liquid being measured has minimal optical density at that wavelength.

By keeping the two wavelengths used in the device relatively close to each other, the impact of wavelength dependent scattering on the measurements at each wavelength can be minimized.

Where the liquid detected is water, said first wavelength is preferably about 1450 nm and said second wavelength is preferably in the range of about 1200 nm to about 1300 nm. Where the liquid detected is condensate, said first wavelength is preferably obtained by sample fluid calibration, and is about 350 nm for the condensate example shown in FIG. 1, and said second wavelength is preferably about 500 nm. Typically where the liquid detected is condensate, said first wavelength is in the range of about 250 nm to 450 nm, and said second wavelength is in the range of about 450 nm to 600 nm.

Preferably the first and second wavelengths are chosen such that there is a difference of at least 2 between the optical density of the liquid at those wavelengths, when measured along a 2 mm optical path length.

Since optical density is measured logarithmically and is proportional to the optical path length, if there is a difference of 2 in the optical density of the liquid at the wavelengths and the path length in question, the absorption at the second wavelength will be $\frac{1}{100}$th of that at the first wavelength, and thus the principal impact on transmittance at the second wavelength will be scattering.

Preferably the light at each wavelength is electronically pulsed or mechanically-chopped and the step of detecting includes using a phase-lock device to lock the frequency of the detected signal at each wavelength to the pulsing or chopping frequency of the emitted signal at the wavelength.

More preferably the light at the first wavelength is pulsed at a different pulse frequency to the light at the second wavelength, thus reducing or eliminating the possibility of interference between the light at the different wavelengths.

A further aspect of the present invention provides a method of measuring the fraction of two liquids in a multi-phase wet-gas flow, including measuring a fraction of a first liquid in accordance with the method of the previous aspect, and measuring a fraction of a second liquid in accordance with the method of the previous aspect.

The or each of the methods of measuring a fraction of a liquid used in the present aspect may include any combination of the optional or preferred features of the methods of the previous aspect.

Preferably the method of the present aspect includes using an apparatus according to the second aspect above, with or without any or all of the preferred or optional features of that aspect.

More preferably, the first liquid is water and the first wavelength used in the step of measuring the fraction of that liquid is about 1450 nm, and the second liquid is condensate and the first wavelength used in the step of measuring the fraction of that liquid is about 350 nm. By measuring the fractions of water and condensate in a multi-phase flow, the total liquid fraction in the flow can be calculated. Such measurements may also be used in calculating overall and individual phase flow rates of the multi-phase flow.

In a development of the above method aspects of the invention, the method further includes the step of detecting a first scattering of light at at least one of said wavelengths at an angle to the transmission path of the light of that wavelength.

The detection of scattered light may be used to correct the level of transmitted light detected, either in addition to or as an alternative to the detection of transmission at another wavelength.

Preferably the development also includes the steps of detecting a second scattering of light at a position downstream of the detection of the first scattered light and measuring cross-correlation between levels of scattered light detected at the two positions.

Cross-correlation of either said second detection of scattering, or of two transmission measurements may be carried out.

The second detection of scattering may be at a different wavelength to that at which the first scattering is detected. For example, in the second of the method aspects above, scattering may be detected at the first wavelengths used to detect each of the liquids. In this way the scattering detection at two positions can be achieved using only the components that are already present in the device.

The measured cross-correlation may be used to determine a flow rate of the wet-gas flow, e.g. by determining the time interval between correlated events and comparing this to the distance between the sensors in question.

A further aspect of the present invention provides a method of determining a flow rate of a wet-gas flow or a component of said wet-gas flow, including the steps of:
  detecting a transmittance or scattering of light at a first position in the wet-gas flow;
  detecting a transmittance or scattering of light at a second position in the wet-gas flow, downstream of said first position;
  cross-correlating the detected transmittance or scattering of light at said first and second positions; and
  calculating said flow rate from said cross-correlation.

Said flow rate may be a flow rate of a liquid film, e.g. on the pipe wall, or a flow rate of liquid entrained in said wet-gas flow. In preferred embodiments, the method determines more than one flow rate which may include either or both of these flow rates.

Preferably the flow is at least 95% gas by volume. As stated above, it may be advantageous at certain flow conditions to combine these aspects of with known flow meters, such as a venturi-type flow meter.

These and further aspects of the invention are described in detail in the following examples and accompanying drawings.

BRIEF DESCRIPTION OF THE DRAWINGS

The invention will now be described, by way of example only, with reference to the accompanying drawings, of which.

DETAILED DESCRIPTION AND EXAMPLES

For fully quantifying the fractions of water and condensate in a gas-condensate well, embodiments of the present invention make optical bulk transmission measurements at two distinctly different narrow-band wavelengths:

At $\lambda \approx 1450$ nm (NIR), water is absorbing, and gas and condensate are transparent. Bulk transmission measurement at this wavelength will lead to water holdup ($\alpha_{water}$)

At $\lambda \approx 350$ nm (UV), condensate is absorbing, and gas and water are transparent. Bulk transmission measurement at this wavelength will detect the presence of condensate; measurement of its holdup ($\alpha_{condensate}$) is possible if the condensate is well characterized at the selected wavelength (which can be achieved e.g. by calibration by using an optical sensor sample cell of 1 mm path length with the target condensate).

In the embodiments of the present invention, correction to the possible loss of transmission energy due to scattering by liquid droplets in the wet-gas flow (particularly in mist or annular-mist flow regimes), is provided by transmission measurements at other wavelengths. For example a further transmission measurement at a wavelength near 1450 nm for better water quantification (e.g. at 1200 nm where water is much less absorbing than at 1450 nm), and a further transmission measurement at a wavelength near 350 nm for better condensate detection (e.g. at around 500 nm).

Fluorescence sensing beyond 350 nm can also aid the detection of condensates and the discrimination from water. See for example Schlumberger's Composition Fluid Analyser (CFA) for use in MDT, S. Betancourt et al. "Analyzing hydrocarbons in the borehole" Oilfield Review (2003 Autumn), p 54.

Figure 2A:
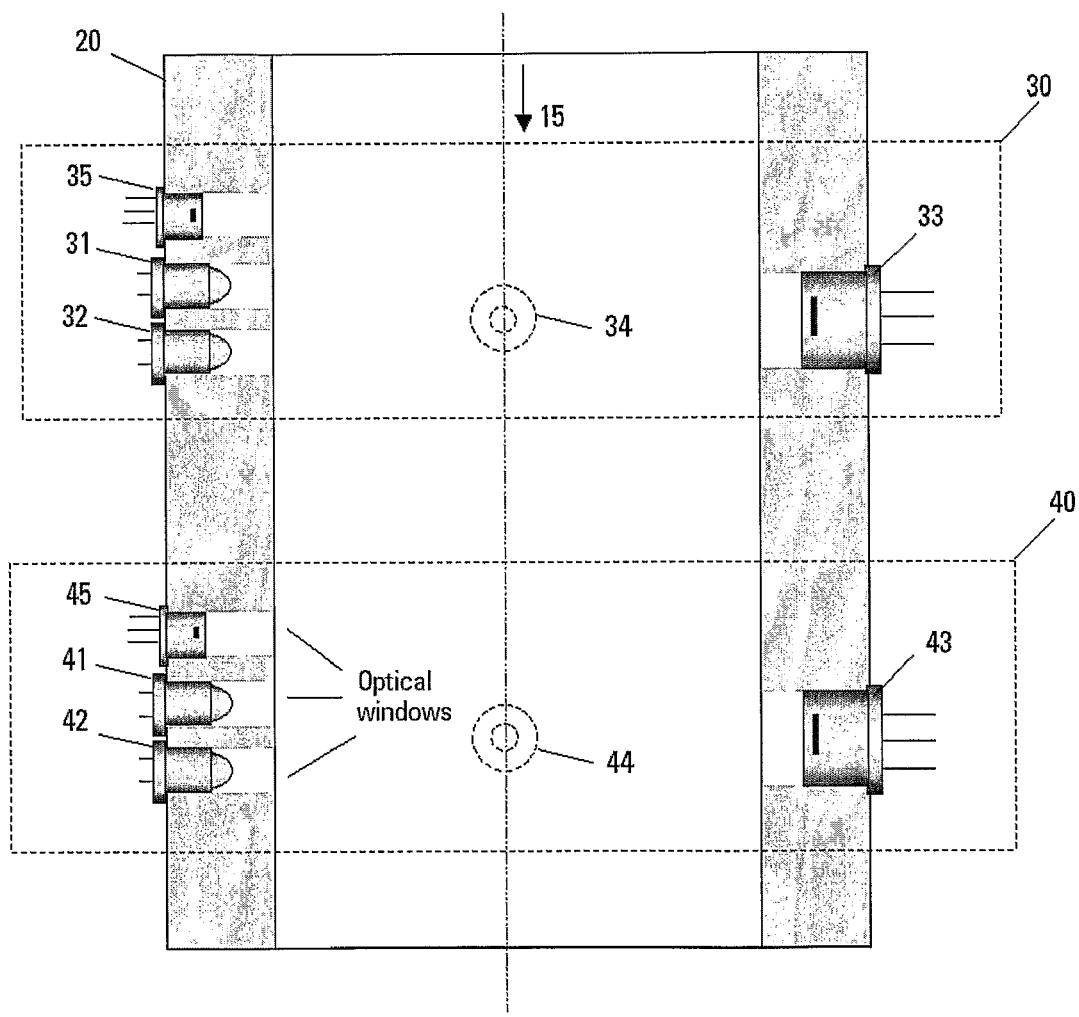
FIG. 2A shows a schematic vertical cross-section of a device according to a first embodiment of the present invention.
Figure 2B:
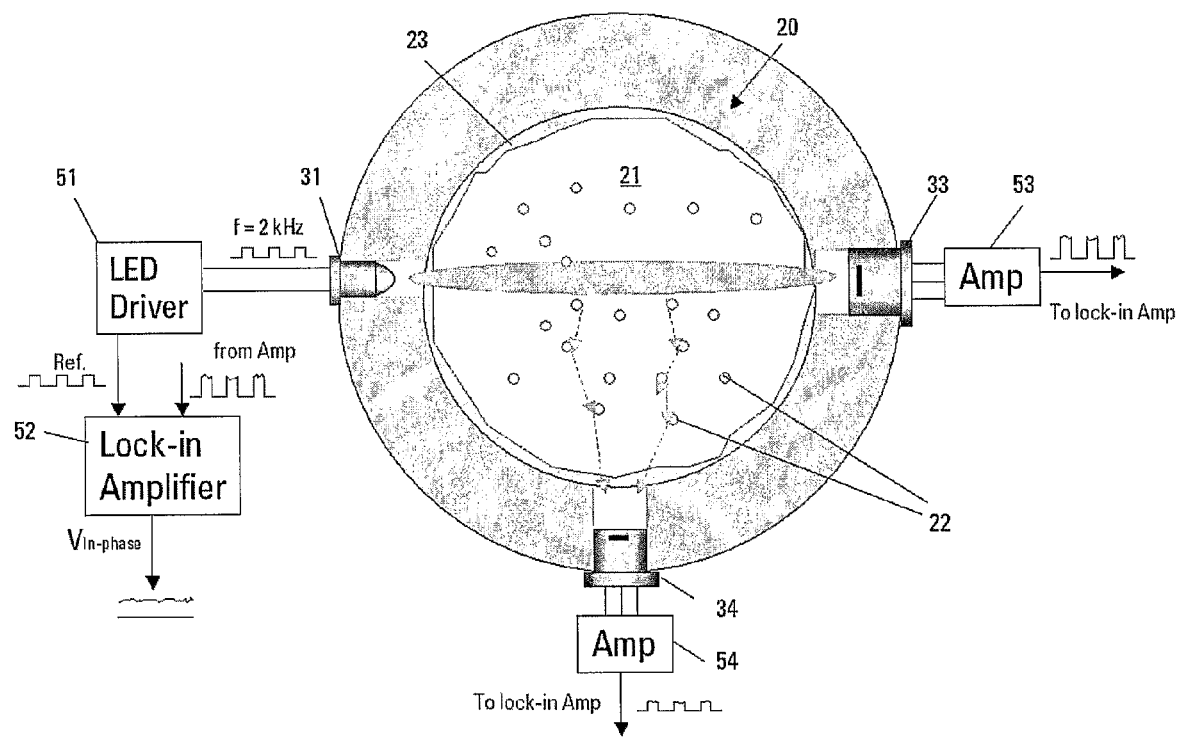
FIG. 2B shows a schematic horizontal cross-section of a device according to a first embodiment of the present invention.

To demonstrate the capability of the water detection unit, optical transmission and scattering measurements of air/water wet-gas downward flows in a 2 inch pipe at narrow-band wavelengths $\lambda_1=1450$ nm and $\lambda_2=1200$ nm have been made (FIG. 4), using the arrangement shown in FIGS. 2A and 2B.

FIG. 2A shows a cut-through side view of a section of piping 20 to which a first embodiment of a measuring apparatus according to the present invention is attached. A wet gas flow passes through the piping 20 in the direction shown by arrow 15.

The measuring apparatus has a number of light-emitting diodes (LEDs) and photodiodes (PDs) arranged along the section of piping 20.

A water detection unit 30 has two near infrared (NIR) LEDs 31 and 32 with narrowband emission characteristics at different wavelengths: LED 31 emits at peak wavelength $\lambda=1450$ nm (water absorbing) and LED 32 emits at peak wavelength $\lambda=1200$ nm (water much less absorbing). Ideally the narrowband emission characteristics of the LEDs are such that their full-width at half maximum (FWHM) is 100 nm or less.

The water detection unit 30 has three PD detectors in the NIR range: transmission detector PD(180°) 33, scattering detector PD(90°) 34 and reflection detector PD(0°) 35. For water fraction determination, the transmission signal measured by the transmission detector PD(180°) 33 at $\lambda=\sim1450$ nm is corrected for the scattering effect by the transmission signal measured by the same PD(180°) 33 at $\lambda=\sim1200$ nm.

The scattering detector PD(90°) 34 is used for liquid droplet detection and droplet velocity measurement (by, for example, cross-correlating with that from the condensate detection unit 40—see below).

A condensate detection unit 40 has two LEDs 41 and 42 with narrowband emission characteristics at two different wavelengths: LED 41 emits UV light at $\lambda=\sim350$ nm (condensate absorbing) and LED 42 emits green light at $\lambda=\sim500$ nm (condensate much less absorbing).

The condensate detection unit 40 also has three PD detectors in the UV/visible range: transmission detector PD(180°) 43, scattering detector PD(90°) 44 and fluorescence & reflection detector PD(0°) 45.

For condensate fraction determination, the transmission signal measured by the transmission detector PD(180°) 43 at $\lambda=350$ nm is corrected for the scattering effect by the transmission signal measured by transmission detector PD(180°) 43 at $\lambda=500$ nm.

The smoothness of the pipe wall of the sensor section should be adequately reduced to minimize adverse reflections from the pipe wall. This can be achieved by appropriate selection of the interior surface, or by mechanical roughening. In the present example, the natural smoothness of the pipe wall of the sensor section is reduced by sanding to minimize reflections from the pipe wall. Ideally total optically absorbing pipe-wall material is used for the optical sensor section.

The scattering detector PD(90°) 44 is used for liquid droplet detection and droplet velocity measurement (by cross-correlating with that from the water detection unit 30).

The liquid droplet velocity derived by cross-correlation of the signals from the two scattering detectors, or from the two transmission detectors is expected to be close to the carry-phase gas velocity, when the gas density is high and droplet size small.

Cross-correlation of the signals from the two reflection detectors could yield the slow-moving liquid film velocity (reflection measurements are more sensitive to the wall-film inhomogeneities).

FIG. 2B is a cross-sectional plan-view of the apparatus of the first embodiment taken at the water detection unit 30. The wet-gas flow in the pipe 20 is shown schematically as being made up principally of gas 21, containing a number of water droplets 22 and with a water film 23 formed on the interior surface of the pipe 20. LED driver 51 and amplifiers 53 and 54 (connected to PDs 33 and 34 respectively) are connected to a lock-in amplifier 52 which allows spurious signals and noise to be reduced or eliminated, ultimately producing an in-phase detection voltage signal $V_{in-phase}$. For the experiments conducted, the pipe section material is infra-red opaque with an inner diameter D=54.8 mm. LED 31 used in the results illustrated was a Hamamatsu L7850-01 series (InGaAs), with peak emission wavelength at 1450 nm and a glass lens window for narrow directivity. LED 32 was a Roithner Lasertechnik LED1200-35M32 (InGaAs), with peak emission wavelength 1200 nm and spherical glass lens. The LED driver 51 was a Roithner Lasertechnik Model D-31, providing variable pulse duration, repetition rate and current amplitude.

Photo-diodes 33, 34 and 35 were Hamamatsu G8370 series, InGaAs PIN photo-diodes, with active areas at ϕ5 mm, ϕ3 mm and ϕ1 mm, respectively. These have a photo-sensitivity in the spectral range 1000 nm to 1600 nm and are optimized for a 1550 nm peak. Amplifiers 53 and 54 were Hamamatsu C4159-03 series amplifiers for infrared detector (InGaAs), having DC to 15k Hz frequency response and providing three ranges of conversion impedance ($10^7$, $10^6$, $10^5$). Lock-in amplifier 52 was a Model SR830 from Stanford Research Systems.

Figure 3:
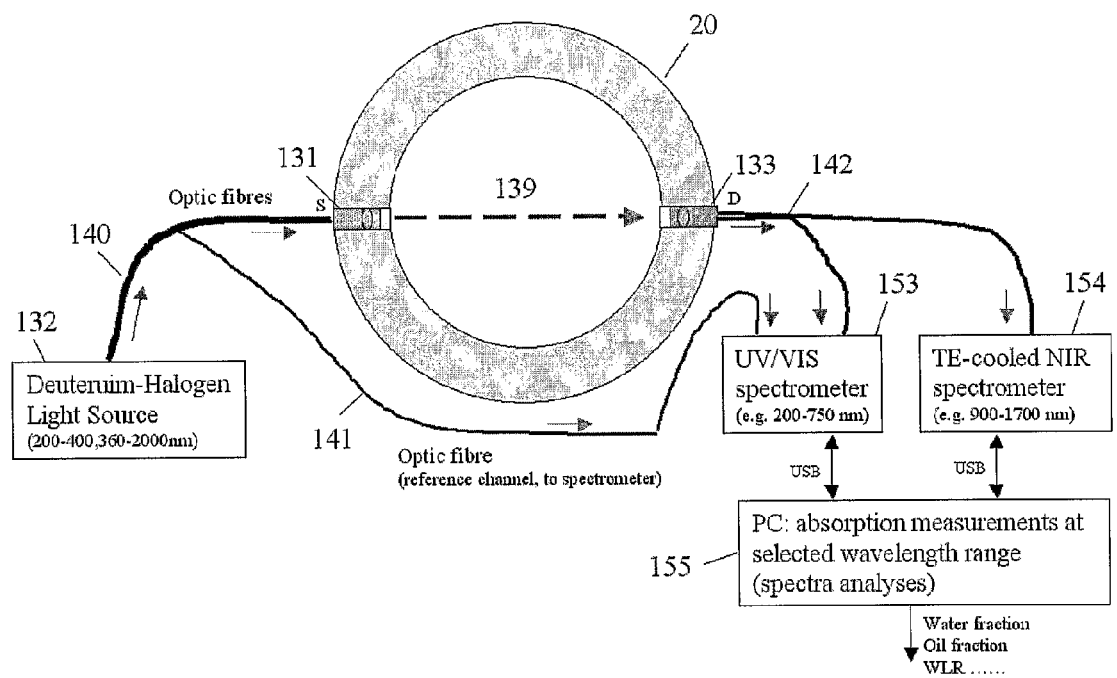
FIG. 3 shows a schematic horizontal cross-section of a device according another embodiment of the present invention.

An apparatus according to an alternative embodiment of the present invention is illustrated in plan view in FIG. 3. To deal with developing/changing wet-gas pipe flows and with the changes in the optical spectral properties of liquid water and especially condensate/oil, as a function of pressure, temperature and time, the apparatus of FIG. 3 provides rapid optical spectroscopic measurement over a selected UV/VIS/NIR range. The measurement is performed along a single optical path 139 across the diameter of pipe 20, through a single pair of transmitting 131 and receiving 133 optical (sapphire) windows. A collimating-lens arrangement and fiber-optic light coupling (not shown) are arranged at the transmitting window 131 and the receiving window 133. The cross-pipe collimated optical beam diameter is about few mm.

For situations where a wet-gas flow is not fully developed, the liquid holdup will generally change along the flow pipe axis. Axially-separated dual optical-path transmissions measured at a narrow-band wavelength for each path (e.g. at 1450 and 1200 nm as in the first embodiment above) may result in errors in the final liquid holdup determination. For example, the liquid droplet size generally reduces as flow accelerates axially, thus giving rise to different holdup and different level of scattering.

One of present embodiments addresses this problem by measuring the dual-wavelength attenuation along a single optical path 139, i.e. effectively using combined-LEDs emitting at two narrow-band wavelengths as one light source using a dichroic mirror, with each LED pulsed at different frequencies. One photo-detector (PD) can be used to detect both signals; they are then separated by the corresponding reference frequencies by using dual-channel lock-in amplifier.

The spectroscopic scheme of the present embodiment has the advantages of measuring, along the same path and virtually at the same time, water and oil transmission attenuations caused by absorption and/or droplet scattering, over a range of the selected wavelengths. Better removal of the scattering effect can be achieved for transmission attenuations measured at the selected wavelength channels covering water absorption peak (around 1450 nm) and condensate/oil absorption peak (e.g. around 350 nm for condensate), by using those measured at the nearby selected wavelength channels away from the water peak (e.g. around 1200 nm) and from the condensate/oil peak (e.g. around 500 nm). The arrangement of the present embodiment may also remove, to a large extent, any partial transmission attenuations caused by the optical-window fouling (e.g. by the deposition of particles/droplets) which in the present embodiment will be identical since only a single pair of optical windows are used for all wavelengths. Thus the present embodiment may provide a more accurate determination of wet-gas water and oil holdups, and hence its water-in-liquid ratio (WLR). Spectroscopic measurements at the selected wavelength region of interest (to allow for rapid spectra data scanning) can also help detect and hence define changes in the water (molecular) absorption peak nominally around 1450 nm and the condensate/oil absorption peak at a wavelength in the UV/visible range, nominally determined by performing oil sample spectroscopic (calibration) measurement. This is because the nominal spectral position and amplitude of the water and condensate/oil absorption peaks (measured e.g. at one pressure and temperature) may vary as pressure and/or temperature change (it is known that the condensate/oil color absorption peak will change from well to well, and can also change over time for a given same well).

The condensate (oil) color absorption peak position and magnitude can be determined by UV/VIS spectroscopic calibration measurement performed at line pressure and temperature, e.g. through an active sampling device incorporating an optical sample flow cell with 1 mm optical path length. This will lead to a better determination of the condensate (oil) fraction. By performing NIR spectroscopic measurement of the water sample captured by the same active sampling device with an optical flow cell, the water OH-band absorption peak magnitude shift around 1450 nm wavelength can be better characterized at line pressure and temperature, which can lead to a better determination of the water fraction.

Fiber-optic coupled light sources covering the UV/VIS/NIR range are commercially available. For example source 132 in FIG. 3 is a combined deuterium-halogen light source covering the 215-2000 nm wavelength range (such as AvaLight-DH-S from Avantes www.avantes.com). This source 132 is connected to transmission window 131 by optical fiber bundle 140. Two separate fiber-optic based spectrometers 153 and 154 are provided and connected to the receiving window 133 by optical fiber bundle 142, one covering UV/VIS range (e.g. 200-750 nm) for measuring condensate/oil fraction, and one covering NIR range (e.g. 900-1700 nm) for measuring water fraction (both also available from Avantes). The spectrometers receive a reference feed 141 from the light source, which is used to correct for the light-source intensity variation by a personal computer 155, which also analyses transmission/absorption spectra outputs at selected wavelength channels to produce the water fraction, the oil fraction and the WLR. A range of wavelengths of interest can be selected to speed-up spectroscopic measurement (a full spectral scan over 2048 wavelength-pixels can be normally done in 2 ms). The reference feed 141 can also be used for phase-lock purposes.

An interpretation scheme according to one embodiment of the present invention uses the optical bulk transmission measurements made at two nearby wavelengths (e.g. $\lambda_1$=1450 nm and $\lambda_2$=1200 nm) for chord-average water holdup determination.

In determination of the water holdup, the first consideration which affects the bulk transmission measurement is geometric droplet scattering ($\Lambda$=1).

The transmission signal T attenuates exponentially:

$$T(\lambda) = \frac{V(\lambda)}{V_{air}(\lambda)} \quad [1]$$

$$= \exp[-\{\mu_A(\lambda) + \mu_S(\lambda)\}d]$$

which gives $\alpha_{water}$:

$$\alpha_{water} \approx \frac{d}{D} = -\frac{1}{D}\frac{\ln[T(\lambda_1)]}{\mu_A(\lambda_1)} \quad [2]$$

This results in an overestimation of $\alpha_{water}$ if scattering is not corrected for, since the attenuation reading will include the effects of scattering.

Assuming similar scattering effects at $\lambda_1$ and $\lambda_2$, i.e. $\mu_S(\lambda_1) \cong \mu_S(\lambda_2)$, and with $\lambda_1$ and $\lambda_2$ preferably chosen such that $\mu_A(\lambda_1) \gg \mu_A(\lambda_2)$, $$\frac{T(\lambda_1)}{T(\lambda_2)} \approx \exp[-\{\mu_A(\lambda_1) - \mu_A(\lambda_2)\}d] \approx \exp[-\mu_A(\lambda_1)d] \quad [3]$$

Thus a good estimation of $\alpha_{water}$ can be obtained if the scattering is corrected:

$$\alpha_{water} \approx \frac{d}{D} = -\frac{1}{D}\frac{\ln[T(\lambda_1)/T(\lambda_2)]}{\mu_A(\lambda_1)}. \quad [4]$$

Next there is consideration of Rayleigh droplet scattering (drop size<=wavelength).

$\mu_S(\lambda_1) \cong \Lambda\mu_S(\lambda_2)$ where $\Lambda=(\lambda_2/\lambda_1)^4$ therefore $$\frac{T(\lambda_1)}{T(\lambda_2)^\Lambda} \approx \exp[-\{\mu_A(\lambda_1) - \Lambda\mu_A(\lambda_2)\}d] \quad [5]$$

which gives $\alpha_{water}$:

$$\alpha_{water} \approx \frac{d}{D} = -\frac{1}{D}\frac{\ln[T(\lambda_1)/T(\lambda_2)^\Lambda]}{\mu_A(\lambda_1) - \Lambda\mu_A(\lambda_2)} \approx -\frac{1}{D}\frac{\ln[T(\lambda_1)/T(\lambda_2)^\Lambda]}{\mu_A(\lambda_1)} \quad [6]$$

As above, preferably $\lambda_1$ and $\lambda_2$ are chosen such that $\mu_A(\lambda_1) \gg \mu_A(\lambda_2)$. In the case of $\lambda_1=1450$ nm and $\lambda_2=1200$ nm, $\Lambda=(1200/1450)^4=0.47$.

There is a third scattering process, diffraction scattering, which is in between Rayleigh and geometric scattering. Ignoring this will lead to very large errors. Choosing $\lambda_1$ and $\lambda_2$ as close as possible could minimize such errors. To estimate the variation of the scattering background with wavelength it is feasible to perform a power-law curve fitting to the actual measurements and then correct using that empirically determined quantity. The equations for the correction are very similar to those already given, if a power-law was fitted.

Note that, scattering can be either wavelength-dependent or wavelength-independent depending on the nature and size of the scatter. In Rayleigh scattering, the scattering cross-section $\sigma_{sc}=(7/9)\pi k^4 a^6$; where k=wave-number $\propto \lambda^{-1}$, a=radius of scattering particle.

Due to the significant wavelength dependency of Rayleigh scattering, the wavelength for the non-absorbed, correction light source (e.g. LEDs 32 and/or 42) is preferably chosen to be as close to the wavelength of the absorbed light source (e.g. LEDs 31 and/or 41), whilst still achieving a large disparity in optical densities.

A similar scheme can be used to determine condensate fraction from transmission measurements made at $\lambda_1=350$ nm and $\lambda_2=9$-500 nm.

For the embodiment of FIG. 3, i.e. when employing a broadband or spectroscopic light source, more sophisticated interpretation methods can be used to characterize absorption peak position and magnitude around 1450 nm and 350 nm, for water and condensate respectively, by using for example curve-fitting methods. More sophisticated interpretation methods can also be used to remove the baseline shifts, caused by the scattering, in the water and condensate absorption peaks. The calculation of baseline shift can be better performed by using a range of wavelengths away from the water and condensate peaks, such as a suitable range of wavelengths around 1300 nm for water and around 350 nm for condensate.

Figure 4:
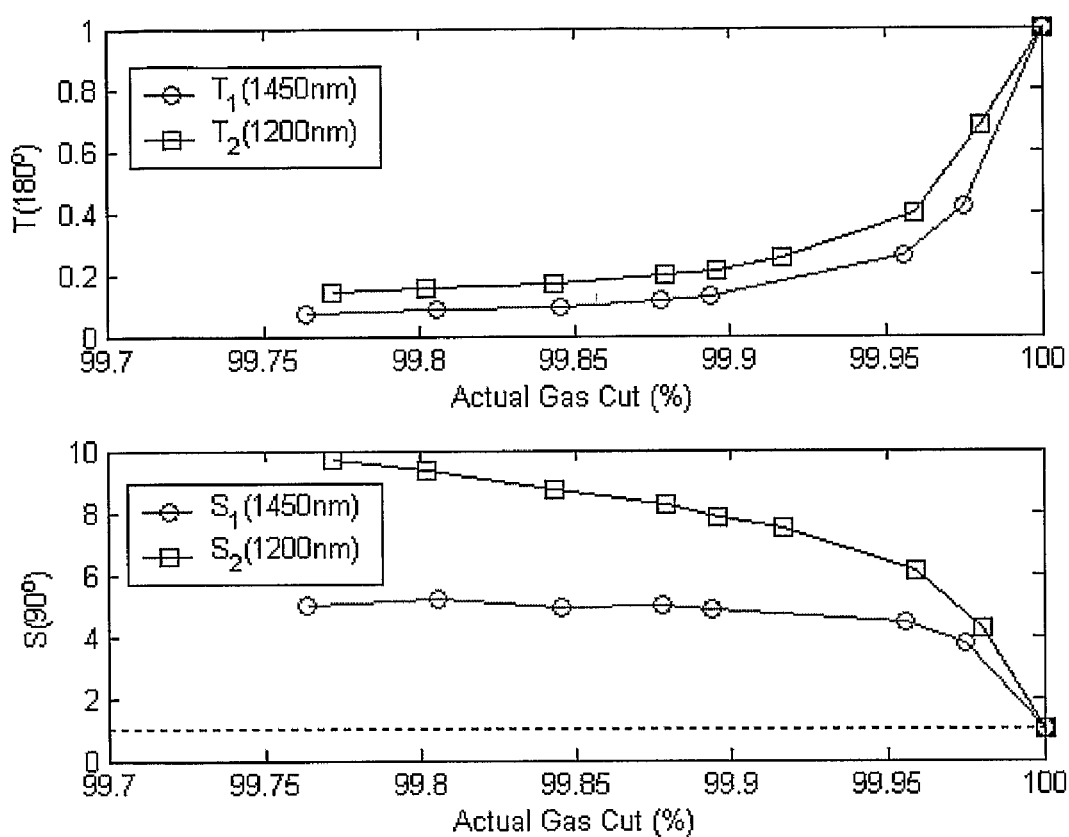
FIG. 4 shows the time-averaged voltage signals of the transmission detector and the scattering detector in examples conducted using the embodiment of FIGS. 2A and 2B.

For the optical arrangement of the embodiment shown in FIGS. 2A and 2B, FIG. 4 gives time-averaged voltage signals ($V_{in\text{-}phase}$) of the transmission PD(180°) 33 and scattering PD(90°) detectors 34, at wavelengths $\lambda_1=1450$ nm and $\lambda_2=1200$ nm, normalized with respect to the respective empty-pipe readings. The air flow rate was largely fixed at 1400 Sm$^3$/h, whilst the water flow rate varied from 0 to 2 m$^3$/h; the actual gas-cut was from 99.75% to 100%.

Figure 5:
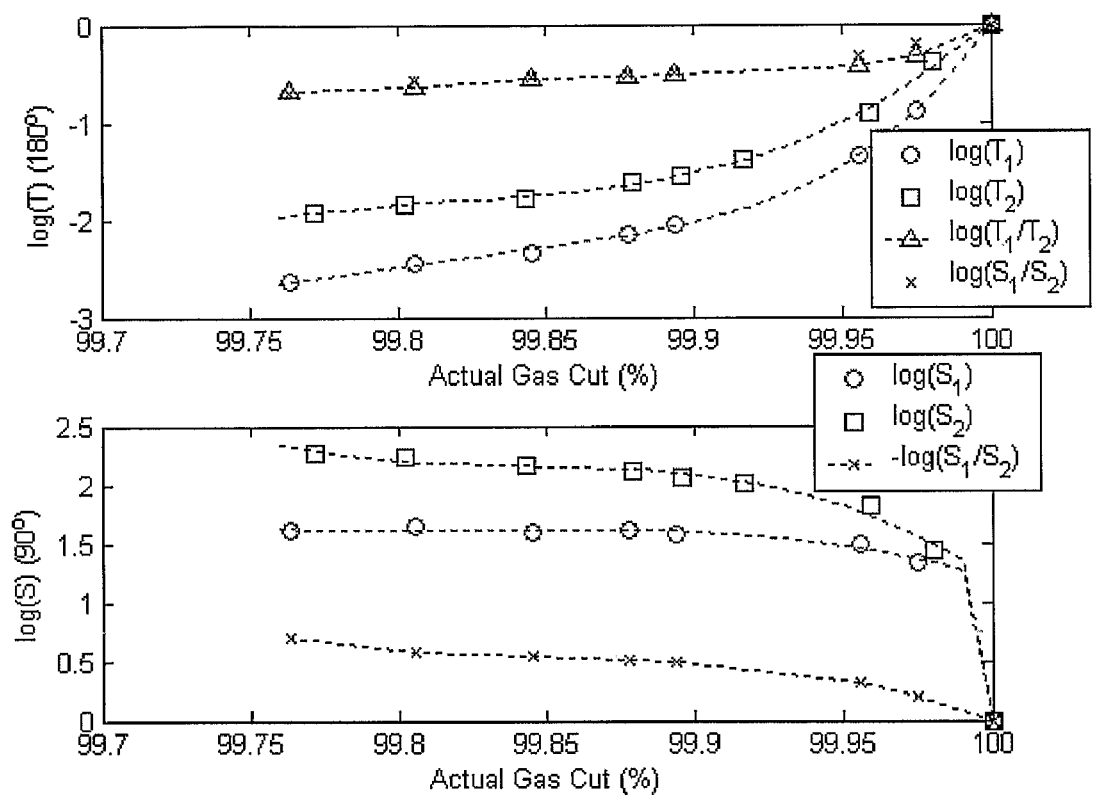
FIG. 5 shows the voltage signals from FIG. 4 normalized with respect to the empty pipe readings and plotted on a log scale along with measurements normalized between the two wavelengths.

FIG. 5 shows a plot vs. the actual gas-cut, of the normalized voltage signals of FIG. 4, further normalized by the respective readings at $\lambda_2$, with the expectation that the scattering effect would be largely removed. This is because, as discussed above, at $\lambda_1$, transmission absorption and scattering effects co-exists, whereas at $\lambda_2$ the scattering effect dominates and absorption contribution is weak (ideally $\mu_A(\lambda_1) \gg \mu_A(\lambda_2)$). Because of the small difference between $\lambda_1$ and $\lambda_2$, we expect that the scattering effects are very similar, i.e. $\mu_S(\lambda_1) \cong \mu_S(\lambda_2)$ when drop-size is significantly larger than the wavelength.

Figure 1:
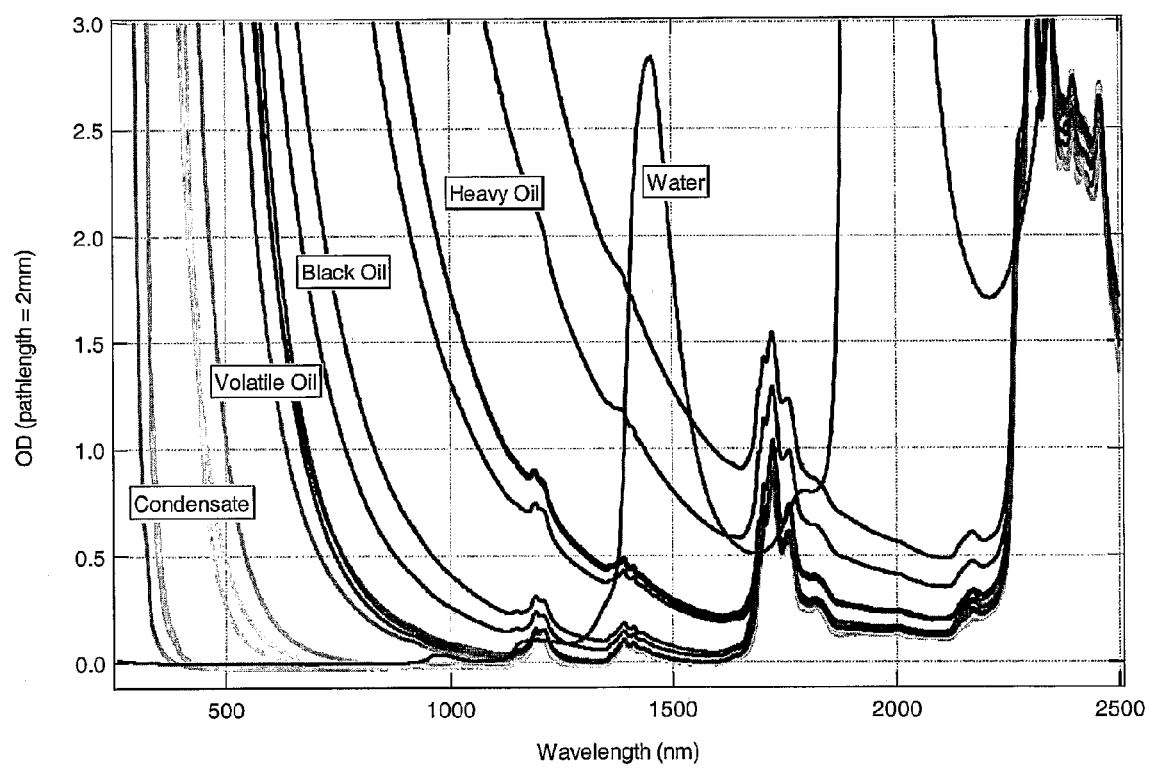
FIG. 1 shows the optical density (OD) measured along a 2 mm optical path length of a variety of fluids found in oilfield situations.

From FIG. 5, it can be seen that the transmission detector signal decreases with increasing water cut (or decreasing gas cut), at both water-absorbing wavelength $\lambda_1=1450$ nm and at the wavelength $\lambda_2=1200$ nm at which water is much less absorbing. At $\lambda_2$, the loss in transmission is mainly due to the light scattering caused by liquid droplets in annular-mist wet-gas flows, since the water is much less absorbing at this wavelength (see FIG. 1). Furthermore, the reduction in the transmission signal is accompanied by the rise in the scattering signal. This is shown by the 90°-scattering detector signal in FIG. 5, which increases with increasing water-cut.

In the lower plot of FIG. 5, the 90° scattering measurements at $\lambda_1$ were also normalized by those at $\lambda_2$ to yield $S_1/S_2$. In the upper plot of FIG. 5 $S_1/S_2$ matches $T_1/T_2$ very well. Hence, after scattering-effect correction, the 90°-scattering detector signal $S_1/S_2$ could also be used to infer liquid holdup (in the scattering path). In a similar manner, it may be possible to use the signal from the reflection detectors 35 and 45 to infer liquid holdup (in the reflection path).

Figure 6:
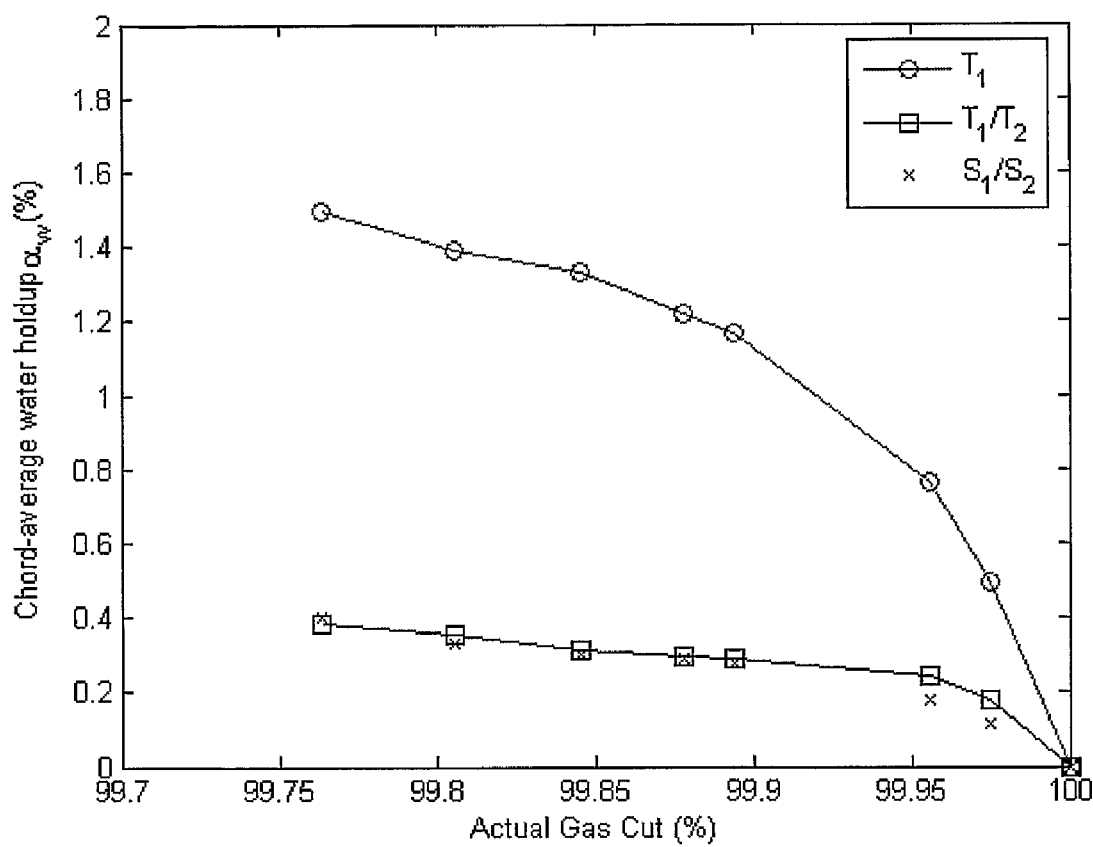
FIG. 6 shows estimates of chord-average water holdup from the data in FIG. 5.

From the data in FIG. 5 (upper plot), FIG. 6 shows the chord-average water holdup estimated from the normalized transmission signal $T_1(\lambda_1)$ (based on equation 2 above), and from $T_1(\lambda_1)/T_2(\lambda_2)$ and $S_1(\lambda_1)/S_2(\lambda_2)$ (based on equation 4 above).

This data shows that, by using NIR optical transmission measurements, water-holdup estimates at very high gas-cuts (here >99.7%) are feasible, and is found to be repeatable. This level of resolution of the optical transmission signals, due to small changes in water holdup in the extremely high gas-cut range, and in a short period of time, has previously not been achievable by using nuclear density-sensing techniques.

The chord-average water-holdup results presented in this invention are based on the <logV(t)> averaging scheme. Chord-average water holdup derived from the log<V(t)> averaging-scheme is equal or smaller than that from the <logV(t)> averaging scheme.

Thus for the embodiment illustrated in FIGS. 2A and 2B above, chord-average water-holdup can be predicted, by correcting the loss of transmission energy caused by scattering of liquid droplets in a wet-gas flow using the transmission measurement at another nearby wavelength of 1200 nm, at which water is much less absorbing. The 90° scattering detector measurements at the dual wavelengths could also be used for water-holdup estimate.

Figure 7:
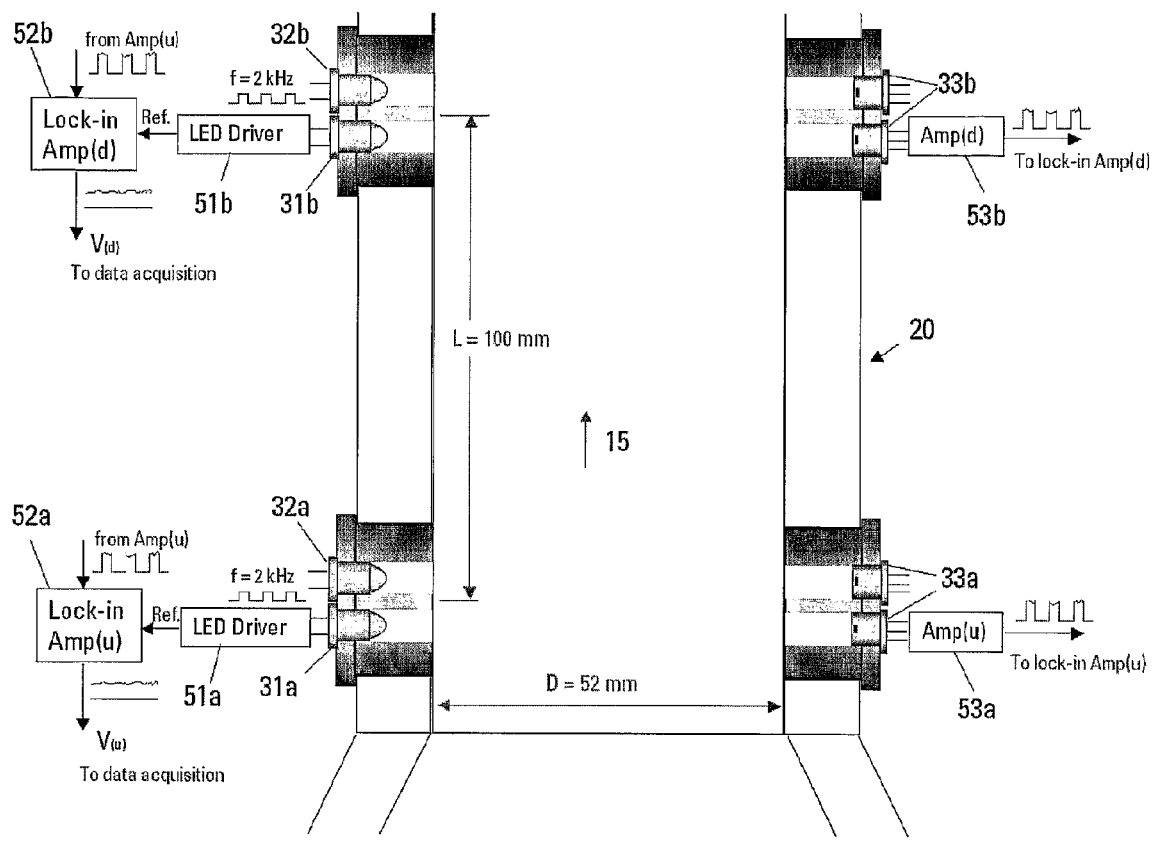
FIG. 7 shows a cross-sectional arrangement of a device according to a further embodiment of the present invention.

FIG. 7 shows an apparatus according to an embodiment of the cross-correlation aspect of the present invention, operating in the NIR range for transmission measurements on an upward gas flow 15 through a 52 mm diameter pipe section 20 which is located at the venturi throat. The axial separation of the NIR sensors is 100 mm.

The reference numerals used in FIG. 7 correspond to the identical elements illustrated in FIGS. 2A and 2B, and these elements will generally not be described further here. However, it will be noted that the apparatus of this embodiment comprises a pair of essentially duplicate detectors, and so corresponding elements of the upstream set have each been given the suffix "a", and those of the downstream set the suffix "b".

Figure 8:
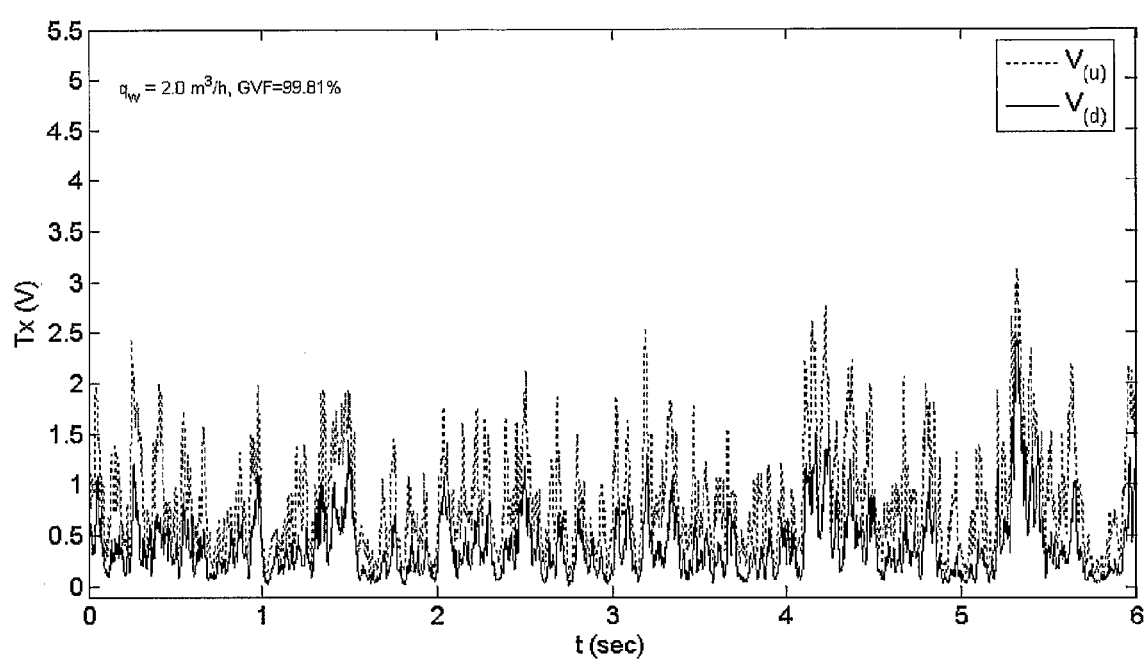
FIG. 8 shows time-traces of the upstream $V_{(u)}$ and downstream $V_{(d)}$ NIR transmission signals at $\lambda=1200$ nm.

In FIG. 8, a set of twin-plane NIR cross-pipe transmission measurement time-traces are plotted for LEDs 32a and 32b and the opposite-facing photo-detectors 33a and 33b operating at a wavelength of $\lambda$=1200 nm, for a gas flow rate $q_G$ at about 1420 Sm$^3$/h and a water flow rate $q_L$ at about 2 m$^3$/h.

Figure 9:
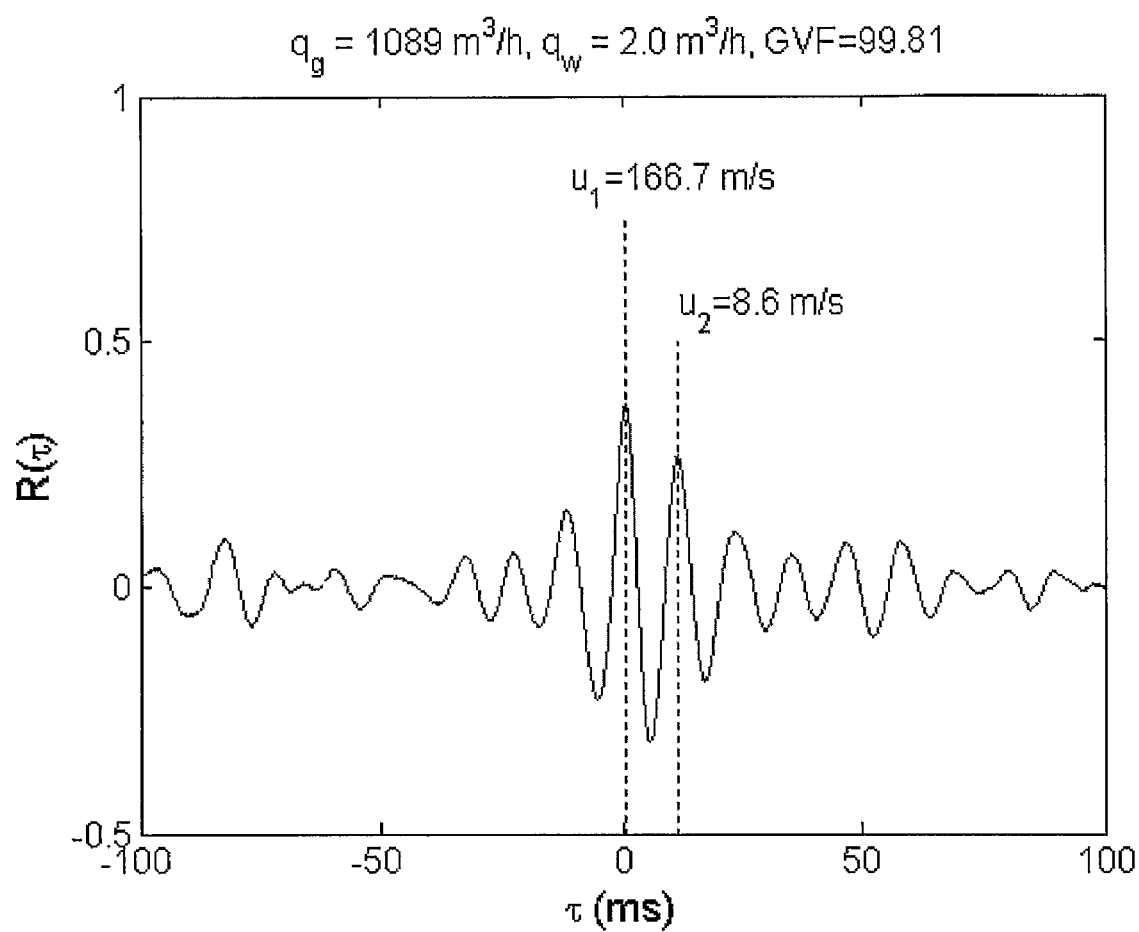
FIG. 9 shows an example cross-correlation of the NIR transmission signals of FIG. 8.

In FIG. 9, an example cross-correlation R($\tau$) of the twin-plane NIR transmission signals shown in FIG. 8 against transit time $\tau$ is shown. Two dominant cross-correlation peaks are marked, which correspond to two flow velocities $u_1$ and $u_2$. The first peak (at a short transit time) corresponds to the fast traveling liquid-drop velocity in the gas core, and the second peak relates to the slow traveling liquid-film velocity on the pipe wall.

Also marked are transit times corresponding to the estimated bulk gas velocity $u_G=q_G/\alpha_G A$ and to the liquid film velocity $u_{LF}=(2\Delta p/\rho_L)^{1/2}$ estimated from the venturi differential pressure $\Delta p$ (A is the pipe area; $q_G$ is the reference gas flow rate; $\alpha_G$ is the gas volume fraction). It can be seen that $u_1$ and $u_2$ match the predicted bulk gas velocity and the liquid-film velocity, respectively, with reasonable accuracy.

Figure 10:
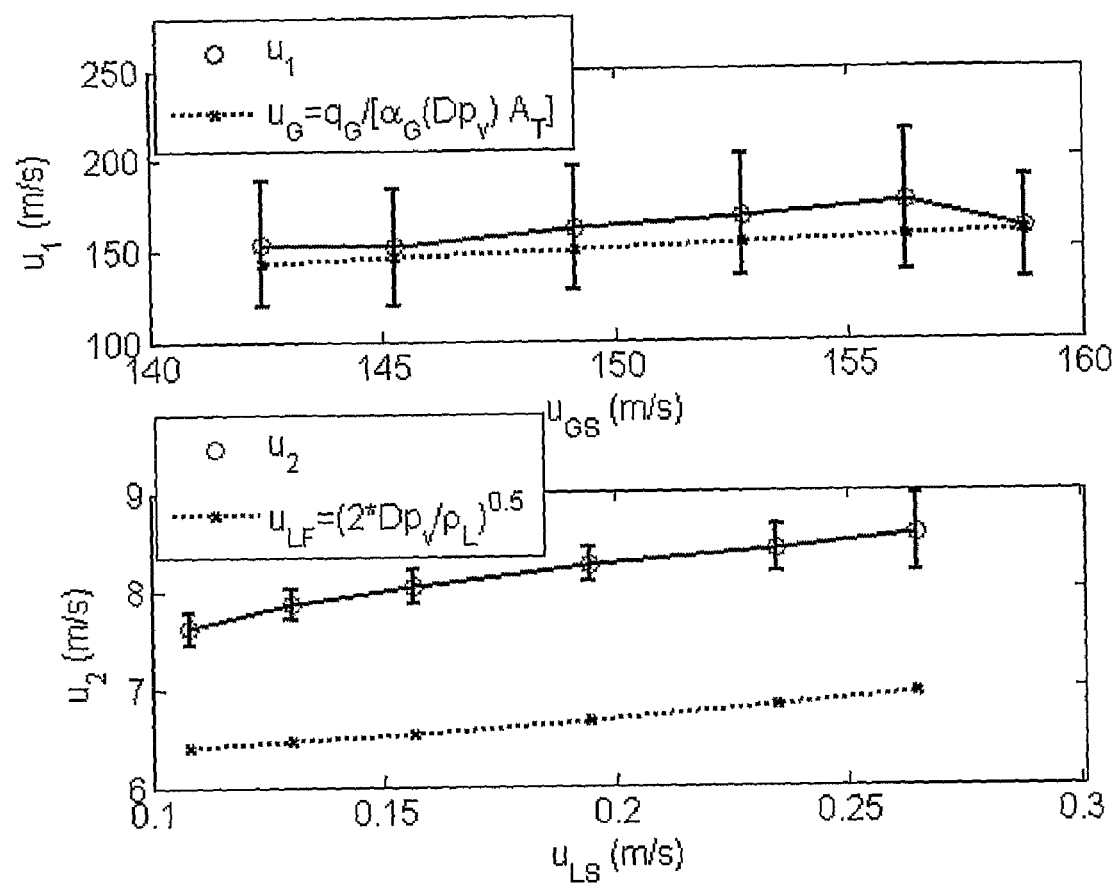
FIG. 10 shows average cross-correlation velocity $u_1$ and bulk gas velocity $u_G$ plotted against superficial gas velocity $u_{GS}$; and the average cross-correlation velocity $u_2$ and liquid-film velocity liquid $u_{LF}$ plotted against superficial liquid velocity $u_{LS}$.

This can be further observed in FIG. 10, the upper plot of which shows the time-average cross-correlation velocity $u_1$ and bulk gas velocity $u_G$ plotted against line-condition superficial gas velocity $u_{GS}$ (measured at an upstream venturi). Similarly, the lower plot of FIG. 10 shows the time-average cross-correlation velocity $u_2$ and liquid-film velocity $u_{LF}$ plotted against the line-condition superficial liquid velocity $u_{LS}$.

It is noted that the cross-correlation velocity $u_2$ is consistently well above the estimated film-velocity $u_{LF}=(2\Delta p/\rho_L)^{1/2}$. The velocity $u_2$ measured by cross-correlation could be the velocity of the waves caused by liquid being ripped off the wall liquid film by the fast traveling gas, which normally travel faster than the film velocity itself. Hence, $u_2$ is generally, an overestimate of liquid-film velocity.

It is also possible to interpret gas and liquid flow rates based on the Smith model (Smith, S. L. "Void fractions in two-phase flow: A correlation based upon an equal velocity head model". *Proc. Instn Mech Engrs* Vol. 184 Pt. 1 No. 36,647-664, 1969), with a known liquid-entrainment factor K (K is estimated to be about 0.95 for flows in FIG. 10), using a liquid-film velocity input from the optical cross-correlation measurement and a liquid-holdup input potentially derived from optical transmission measurements with scattering-effect removal e.g. as discussed in earlier embodiments.

Whilst particular embodiments of the present invention have been set out above, the skilled person will appreciate that these are only exemplary and in particular that modifications and variations can be made to the above embodiments without departing from the scope of the present invention.

The invention claimed is:

1. A device for measuring the fraction of a liquid in a wet gas flow, the device including:
    one or more light sources emitting at a first wavelength at which the liquid is highly absorbing and emitting at a second wavelength close to the first wavelength and at which the liquid is not highly absorbing; and
    one or more sensor for detecting the transmittance of the light at the first and second wavelengths through said gas flow,
    the device further including processing means for determining a liquid fraction of the liquid in the wet gas flow by correcting the transmittance measured at the first wavelength for the effects of scattering using the transmittance measured at the second wavelength;
    wherein the light sources emit in a pulsed fashion and the sensor or processing means includes a phase-lock device to lock the frequency of the detected signal to pulsing frequency of the emitted signal.

2. A device according to claim 1 wherein the light sources emit in a pulsed fashion at different pulse frequencies to each other.

3. A device according to claim 1, further including at least one additional sensor arranged at an angle to the transmission path of at least one of said light sources to detect scattered light.

4. An apparatus for measuring the fraction of two liquids in a multi-phase gas flow, the apparatus including two devices according to claim 1, each of said devices being arranged to detect a respective one of said liquids.

5. An apparatus according to claim 4, the apparatus further comprising a processor adapted to measure the cross-correlation between the levels of light detected at each device.

6. An apparatus according to claim 5 wherein said processor is further adapted to determine a flow rate of the wet-gas flow or a component of the wet-gas flow from said measured cross-correlation.

7. An apparatus for determining a flow rate of a wet-gas flow or a component of said wet-gas flow, including:
    a first light source and a second light source located downstream of said first light source; and
    two or more sensors for detecting the transmittance or scattering of the light from the first and second light sources through said wet-gas flow; and
    cross-correlator for determining said flow rate by cross-correlating the detected transmittance or scattering of light from said first and second light sources.

8. An apparatus according to claim 7 wherein said flow rate is one of a flow rate of a liquid film and a flow rate of liquid entrained in said wet-gas flow.

9. An apparatus according to any one of claims 7 to 8 wherein the correlator is adapted to determine more than one flow rate.

10. An apparatus for measuring the fractions of water and condensate in a multi-phase gas flow, the apparatus comprising:
- a water measuring device comprising
    - one or more light sources emitting at a first wavelength at which water is highly absorbing and emitting at a second wavelength close to the first wavelength and at which water is not highly absorbing; and
    - one or more sensors for detecting the transmittance of the light at the first and second wavelengths through said gas flow; and
- a condensate measuring device comprising
    - one or more light sources emitting at a third wavelength at which condensate is highly absorbing and emitting at a fourth wavelength close to the third wavelength and at which the condensate is not highly absorbing; and
    - one or more sensors for detecting the transmittance of the light at the third and fourth wavelengths through said gas flow;
- the apparatus further including processing means for determining liquid fractions of water and condensate in the wet gas flow by correcting the transmittance measured at the first wavelength for the effects of scattering using the transmittance measured at the second wavelength and correcting the transmittance measured at the third wavelength for the effects of scattering using the transmittance measured at the fourth wavelength.

11. Apparatus according to claim 10 further comprising a processor adapted to measure the cross-correlation between the levels of light detected at the water measuring device and the condensate measuring device and determine a flow rate of the wet-gas flow or a component of the wet-gas flow from said measured cross-correlation.

12. A device for measuring the fraction of a liquid in a wet gas flow, the device including:
- one or more light sources emitting at a first wavelength at which the liquid is highly absorbing and emitting at a second wavelength close to the first wavelength and at which the liquid is not highly absorbing; and
- one or more sensors for detecting the transmittance of the light at the first and second wavelengths through said gas flow,
- at least one additional sensor arranged at an angle to the transmission path of at least one of said light sources to detect scattered light;
- the device including processing means for determining a liquid fraction of the liquid in the wet gas flow by correcting the transmittance measured at the first wavelength for the effects of scattering using the transmittance measured at the second wavelength and also including processing means for measuring the cross-correlation between the levels of light detected at the sensors for detecting transmittance and the additional sensor and determining a flow rate of the wet-gas flow or a component of the wet-gas flow from said measured cross-correlation.

13. An apparatus according to claim 7 wherein said cross correlator determines both a flow rate of a liquid film and a flow rate of liquid entrained in said wet-gas flow.

* * * * *